United States Patent [19]
Fraser

[11] Patent Number: 6,001,559
[45] Date of Patent: *Dec. 14, 1999

[54] **METHOD FOR DETECTING *LISTERIA MONOCYTOGENES* VIA ESCULIN HYDROLYSIS AND NUCLEIC ACID HYBRIDIZATION**

[75] Inventor: Judy A. Fraser, Apple Valley, Minn.

[73] Assignee: The Pillsbury Company, Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 07/912,408

[22] Filed: Jul. 13, 1992

[51] Int. Cl.⁶ .............................. C12Q 1/68; C12P 21/06
[52] U.S. Cl. ................................. 435/6; 435/68.1
[58] Field of Search ................. 435/6, 68.1, 170, 435/240.25

[56] References Cited

U.S. PATENT DOCUMENTS 5,089,386   2/1992   Stackebrandth et al. ................... 435/6

OTHER PUBLICATIONS

Fraser & Sperber, "Rapid Detection of Listeria spp. in Food & Environmental Samples by Esculin Hydrolysis," Journal of Food Protection, vol. 51, #10, pp. 762–765 (1988).
Okumabula, et al. "Evaluation of a Chemiluminescent DNA Assay for the Rapid Detection of *Listeria Monocytogenes*," Research Microbiology, vol. 143, pp. 183–189 (1992).
Accu–Probe "*Listeria Monocytogenes* Culture Identification Test" Protocol (1990).
J. Cin. Microbiol 4(2)[1976]: 180–184.
Edberg, S.C; et al "Rapid Spot Test for the Determination of Esculin Hydrolysis" Proc. Natl. Acad. Sci. U.SA 79:6999–7003 (1982).
Wirth D.F; et al Rapid Identification of Leishmania Species by Specific Hydrization of Kinetoplast DNA in Cutaneous Lesions.

*Primary Examiner*—Eggerton A. Campbell
*Attorney, Agent, or Firm*—Amy J. Hoffman; Janal M. Kalis; Aleya Rahman

[57] ABSTRACT

A method for rapidly detecting non-viral organisms disclosed. The method involves pelleting an enrichment culture of a sample, optionally washing the pellet, resuspending the pellet in an appropriate reagent before performing a nucleic acid hybridization confirmation test on the sample.

3 Claims, 2 Drawing Sheets

METHOD FOR DETECTING *LISTERIA MONOCYTOGENES* VIA ESCULIN HYDROLYSIS AND NUCLEIC ACID HYBRIDIZATION

FIELD OF THE INVENTION

The present invention deals with detecting non-viral organisms. Specifically, the invention is a method of rapidly obtaining a culture suitable for detecting pathogens via a DNA probe. The method of the invention saves both time and money as compared to currently used DNA probe detection methods and more conventional procedures used by the FDA and the USDA such as biochemical and physiological methods. The method of the invention may be used to obtain a culture to detect the presence of pathogens or any non-viral organism in areas such as medical, veterinary, and agricultural diagnostics; industrial and pharmaceutical quality control.

BACKGROUND OF THE INVENTION

Bacterial pathogens can cause severe illness and even death if they are ingested by animals or humans. Detecting pathogens is critical in the food industry because foodborne pathogens infect unsuspecting consumers. Quality assurance tests must be done before food is shipped to ensure that pathogens are not present. Quality assurance tests, including environmental tests, must also be performed on an ongoing basis during production to ensure that the food is not contaminated during processing.

Traditional techniques for identifying pathogens are complicated and are time and labor intensive. Recently developed identification techniques utilize DNA probes and rely on the ability of complimentary nucleic acid strands to specifically align and associate to form stable double-stranded complexes. Although nucleic acid hybridization techniques greatly reduce the time required to identify pathogens as compared to physiological and biochemical methods; hybridization methods still require a culture suitable for testing. The process for obtaining a suitable culture is lengthy. It is the object of the present invention to reduce the amount of time and money required to obtain a suitable culture for detecting pathogens via nucleic acid hybridization techniques.

A common contaminant of the environment in food processing plants and some foods is *Listeria monocytogenes* which may cause death if immunosuppressed individuals ingest the bacteria. The current most conclusive method for detecting *L. monocytogenes* uses a DNA probe. The current method for obtaining a culture suitable for nucleic acid hybridization confirmation techniques is commonly known in the art and is diagrammed in FIG. 1. To obtain a suitable culture, a sample from a suspect food or environmental source is placed in a broth to obtain a primary enrichment. A primary enrichment broth is one which contains many nutrients and may not be selective for the suspect organism. If one is testing for the presence of *L. monocytogenes*, an example of a broth suitable for a primary enrichment is University of Vermont Media (UVM as available from Difco of Detroit, Mich.). The inoculated primary enrichment broth is incubated for about 24 hours at about 30° C.

After incubation, the primary enrichment may be used to inoculate a broth for a secondary enrichment. Secondary enrichment broths are preferably selective or presumptively differential for the organism being detected. Not all organisms require a secondary enrichment and one skilled in the art will be able to determine whether or not the suspect organism requires a secondary enrichment for detection purposes.

If one is testing for *L. monocytogenes*, a secondary enrichment is necessary and Fraser Broth is a suitable secondary enrichment broth. For *L. monocytogenes*, the secondary enrichment is incubated for about 24 to about 28 hours at about 35° C. Fraser and Sperber, "Rapid Detection of Listeria spp. in Food & Environmental Samples by Esculin Hydrolysis," *Journal of Food Protection*, Vol., No. 10, pp. 762–765 (October '88) discusses the efficacy of Fraser Broth for the presumptive detection of Listeria species. The Fraser and Sperber article is herein incorporated by reference. The screening with Fraser Broth allows the technician only to test samples which presumptively contain *L. monocytogenes*, positive samples turn Fraser Broth dark brown or black.

The presumptively positive secondary enrichment samples are next streaked onto plates. When testing for *L. monocytogenes*, a suitable plating medium is Listeria Plating Medium (LPM) (Difco). The plates are then incubated for about 48 hours at about 35° C. Colonies which are suspected to be *L. monocytogenes* are picked and streaked onto Trypticase Soy Agar with 0.6% Yeast Extract plates (TSA-YE) (Difco) which are incubated for about 24 to 48 hours at about 35° C. After the lengthy foregone procedure, the sample is finally ready for identification via nucleic acid hybridization. The procedure takes at least about 4 and up to about 6 days to complete. During this preliminary incubation and screening, people may be eating food contaminated with *L. monocytogenes* which poses health risks. Alternatively, production of foods may be halted which is expensive. Both of these consequences are unacceptable.

As further shown in FIG. 1, a nucleic acid hybridization which is a conclusive identification test may be performed on a culture obtained from the above-described procedure. The ACCUPROBE™ *L. monocytogenes* Culture Confirmation Test assay procedure sold by Gen-Probe® of San Diego, Calif. gives the following protocol for nucleic acid hybridization. The ACCUPROBE™ procedure, which is herein incorporated by reference, involves a Sample Preparation, Hybridization, Selection, and a Detection Step. The first step is the Sample Preparation Step. Fifty microliters of 0.04% sodium azide solution (Reagent 1 as purchased in the ACCUPROBE™ *L. monocytogenes* Culture Confirmation Test—hereinafter "ACCUPROBE™ Kit") is added to lyophilized nucleic acid which is specific for the organism to be identified. One microliter loopful of cells from the LPM plates is also added to the Reagent 1 tube. The above combination is incubated for about 5 to 10 minutes at about 35 to 37° C. to lyse the cells.

After the Sample Preparation, the Hybridization step is performed. Fifty microliters of Reagent 2, which is identified only as a "Buffered Solution" in the AccuProbe™ Kit, is added to the combination. This is incubated for about 15 minutes at about 60° C.

The Selection Step follows the Hybridization Step. The Selection Step includes adding about 300 microliters of Reagent 3 (identified only as the "Selection Reagent" in the ACCUPROBE™ Kit and corresponding protocol) to the combination and incubating for about 5 minutes at about 60° C. After allowing the tubes to equilibrate at room temperature for about 5 minutes, the samples are read in a Luminometer as can be purchased from Gen-Probe® and any samples having a reading of 50,000 Relative Light Units (RLU) on the Leader model Luminometer or more is deemed positive or about 1500 RLU or more on the PAL model Luminometer is deemed positive.

The ACCUPROBE™ single-stranded DNA probe uses a chemiluminescent label. Once the bacteria have lysed, the ACCUPROBE™ DNA strand is free to hybridize with the bacterial ribosomal RNA and form a stable DNA:RNA hybrid. The detection reagents which are hydrogen peroxide in nitric acid and a 1N solution of sodium hydroxide allow for the differentiation between the hybridized and non-hybridized probe and only those which have hybridized luminesce. This chemiluminescence reaction is fully described in Okwumabua, et al, "Evaluation of a Chemiluminescent DNA Probe Assay for the Rapid Confirmation of *Listeria monocytogenes*," *Research Microbiology* (1992) Vol. 143, pp. 183–189 which is herein incorporated by reference.

DNA probes used to detect pathogenic bacteria may be purchased from Gen-Probe® of San Diego, Calif. Currently available DNA probes include tests for Campylobacter, Enterococcus, Haemophilus influenzae, Neisseria gonorrhoeae, Staphylococcus aureus, Group A and Group B Streptococcus, Streptococcus pnumoniae, and of course, *L. monocytogenes*. The method of the present invention may be used with any existing DNA probe to reduce the time and labor required to identify non-viral organisms. Alternatively, one may develop DNA probes specific for the suspect organism by following the disclosure in U.S. Pat. No. 4,851,330 which is herein incorporated by reference.

SUMMARY

The invention allows saving of time and money when identifying non-viral organisms. The present invention accomplishes this by eliminating steps traditionally required to obtain a suitable culture for nucleic acid hybridization confirmation tests. The invention involves centrifuging an enrichment culture, decanting the supernatant, optionally washing the pellet, and then proceeding with a nucleic acid hybridization identification. This procedure eliminates plating of the culture and omits at least 2 days of culture preparation time.

A further aspect of the invention arises in the confirmation test step. If the ACCUPROBE™ *L. monocytogenes* Culture Confirmation Test is used, the invention modifies the published protocol. The procedure of the invention differs from the ACCUPROBE™ procedure only in that 75 microliters of Reagent 1 is used to resuspend a pellet obtained from centrifuging 1 ml of Secondary Enrichment Broth instead of 50 microliters as called for in the ACCUPROBE™ protocol. When detecting whether or not the organism is present, a reading of about 500 RLU on the PAL model Luminometer is deemed positive when practicing the procedure of the invention.

DETAILED DESCRIPTION OF THE INVENTION

Figure 1:
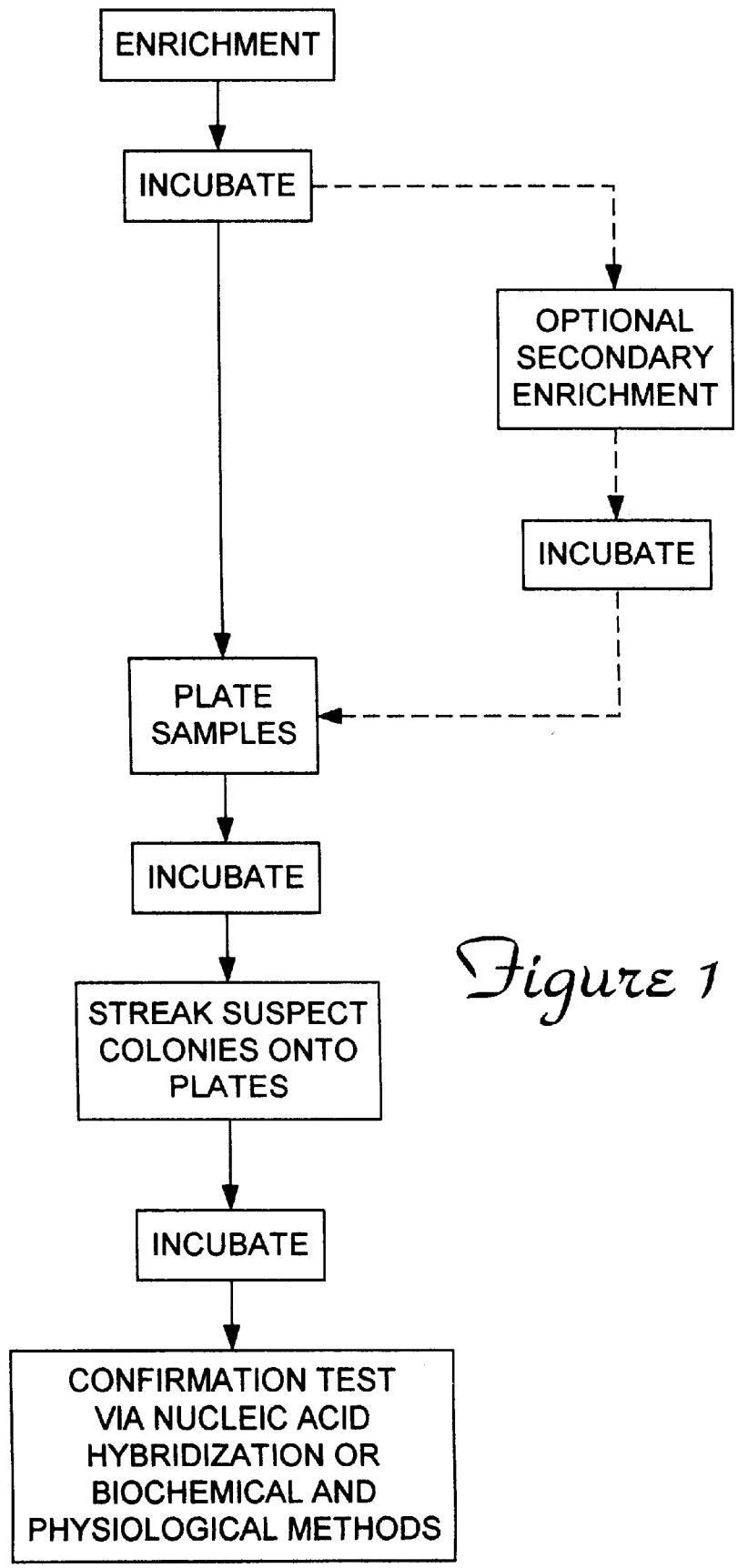
FIG. 1 is a schematic of the prior art method of obtaining a suitable culture for detecting non-viral organisms.
Figure 2:
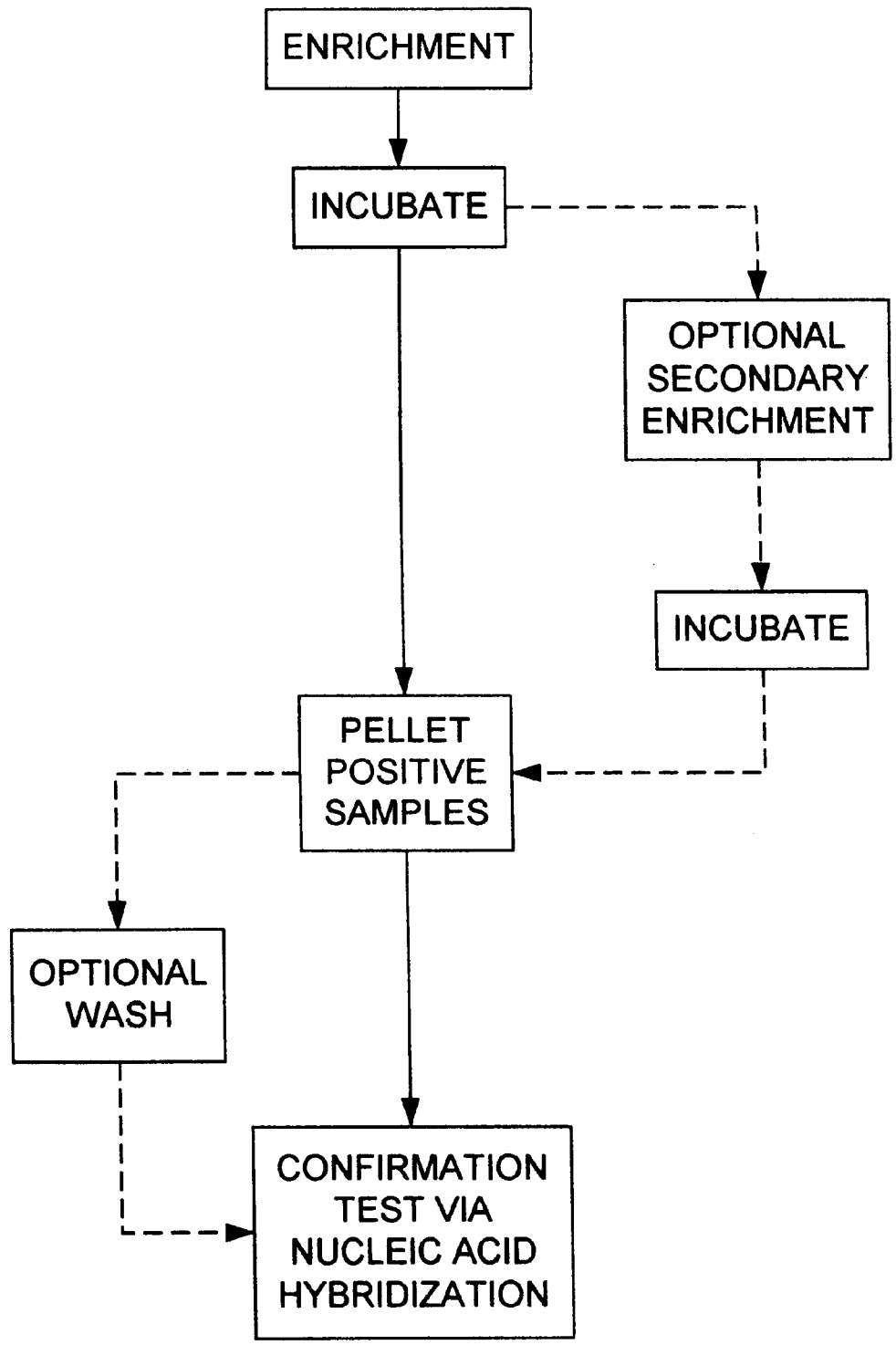
FIG. 2 is a schematic of the method of the present invention for obtaining a suitable culture for detecting non-viral organisms.

According to the invention, enrichment culture tubes are individually centrifuged until a pellet of cells is formed. The enrichment tubes may contain either a primary or secondary enrichment culture depending upon the detection requirements of the suspect organism. For purposes of detecting *L. monocytogenes*, a secondary enrichment is necessary and the preferred secondary enrichment is Fraser Broth. Thus, according to the invention, tubes of Fraser Broth which reflect a positive or presumptively positive reading are centrifuged. Fraser Broth tubes which turn dark brown or black are deemed to be presumptively positive. Preferably about 1.0 ml of the enrichment culture is placed in a microcentrifuge tube and spun at about 13,000 rpm in a Biofuge 13 microcentrifuge sold by Scientific Products of Mc Gaw Park, Ill. or about 14,926×G for about 3 minutes to obtain a pellet.

The pellet may then be washed. One skilled in the art may decide whether or not a wash is necessary. Without intending to be bound by theory, it is believed that the wash removes the residual enrichment broth and eliminates any interference which may result from the broth in later Detection steps. A wash step is necessary if Fraser Broth is used to grow *L. monocytogenes* because presumptively positive tubes turn dark brown or black in color. This dark coloring conceals the luminescence of the hybridized samples in the Detection step of the ACCUPROBE™ method.

Although any washing agent may be used, an example of a suitable washing agent is a phosphate buffer such as Butterfield's Phosphate Buffer as can be purchased from Difco. If a wash is necessary, preferably about 0.5 ml of Butterfield's Phosphate Buffer is used to wash the pellet. The wash may involve resuspending the pellet in the Buffer and then centrifuging as described above to repellet the cells and then decanting the supernatant. Preferably the Buffer is merely passed over the pelleted cells without resuspending the pellet and then the Buffer is decanted. Following the wash step, the culture is now ready for nucleic acid hybridization techniques.

The above-described procedure of the invention eliminates the plating of suspect cultures after the Enrichment. Thus, a *L. monocytogenes* culture suitable for nucleic acid hybridization detection techniques is obtained in merely two days according to the method of the invention as compared to the prior art method which takes at least 4 and up to about 6 days to obtain a suitable culture.

Following centrifugation and washing of the pellet, a nucleic acid hybridization may be performed on the culture. An example of a nucleic acid hybridization procedure for detecting *L. monocytogenes* is the ACCUPROBE™ Culture Confirmation Test. A pellet obtained from about 1 ml of Secondary Enrichment Broth should be resuspended in about 75 microliters of an appropriate buffer. If the ACCUPROBE™ Kit is used, an appropriate buffer is Reagent 1 as purchased in the Kit. This is a modification of the protocol as published by Gen-Probe® and this amount may vary depending upon the size of the pellet obtained from centrifuging.

After the slight modification of the amount of Reagent 1 used, the ACCUPROBE™ Kit protocol is then followed for detecting *L. monocytogenes* until the Detection Step. When practicing the method of the present invention, a reading of about 500 RLU on the PAL model Luminometer or greater is considered confirmed positive whereas signals of less than about 500 RLU are negative. Alternatively, one may repeat any tested samples which have readings between about 400 and about 500 RLU to ensure a correct result is obtained.

One skilled in the art will recognize that the method of the present invention may be used to detect any non-viral organism using a nucleic acid hybridization technique. It will likewise be apparent to one skilled in the art that any nucleic acid hybridization protocol may be followed in conjunction with the present invention.

We claim:

1. A method for rapidly detecting *Listeria monocytogenes*, comprising:

obtaining a sample comprising *Listeria monocytogenes*;

culturing the sample in an enrichment media;

identifying esculin hydrolysis by *Listeria monocytogenes* in the cultured sample;

centrifuging the enrichment media to obtain a pellet comprising *Listeria monocytogenes*;

resuspension; and detecting *Listeria monocytogenes* in the resuspended pellet with a single-stranded DNA probe that has a chemiluminescent label.

2. The method of claim 1 and further including washing the pellet prior to resuspension.

3. The method of claim 1 wherein the enrichment media is Fraser broth.

* * * * *